US006316381B1

(12) United States Patent
Auer et al.

(10) Patent No.: US 6,316,381 B1
(45) Date of Patent: *Nov. 13, 2001

(54) MULTIMETALLIC CATALYST AND PROCESS FOR PREPARING SUBSTITUTED AROMATIC AMINES

(75) Inventors: Emmanuel Auer, Frankfurt; Andreas Freund, Kleinostheim; Michael Gross, Frankfurt; Rolf Hartung, Neuberg, all of (DE)

(73) Assignee: Degussa AG, Hanau (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/895,204

(22) Filed: Jul. 16, 1997

(30) Foreign Application Priority Data

Jul. 23, 1996 (DE) ............................................... 196 29 659
Sep. 6, 1996 (DE) ............................................... 196 36 214

(51) Int. Cl.$^7$ ..................................................... B01J 23/34
(52) U.S. Cl. ........................................... 502/185; 502/324
(58) Field of Search ..................................... 502/241, 245, 502/259, 260, 261, 184, 185, 324, 326, 327, 331, 325, 332

(56) References Cited

U.S. PATENT DOCUMENTS

| 3,253,039 | | 5/1966 | Rylander | 260/580 |
|---|---|---|---|---|
| 4,018,670 | | 4/1977 | Sinfelt | 208/140 |
| 4,122,671 | * | 10/1978 | Armstrong et al. | 502/185 |
| 4,124,538 | | 11/1978 | Armstrong et al. | 252/466 |
| 4,132,672 | | 1/1979 | Wise et al. | 252/466 |
| 4,184,983 | * | 1/1980 | Ritz et al. | 423/219 |
| 4,760,187 | | 7/1988 | Kosak | 564/417 |
| 4,977,036 | * | 12/1990 | Baldi | 428/553 |
| 4,994,247 | | 2/1991 | Tooley et al. | 423/247 |
| 5,102,851 | | 4/1992 | Eri et al. | 502/302 |
| 5,105,012 | | 4/1992 | Theodoridis | 564/417 |
| 5,192,452 | | 3/1993 | Mitsui et al. | 210/760 |
| 5,232,886 | * | 8/1993 | Yoshimoto et al. | 502/185 |

FOREIGN PATENT DOCUMENTS 1453966  10/1976  (GB).

* cited by examiner

Primary Examiner—Stuart L. Hendrickson
(74) Attorney, Agent, or Firm—Smith, Gambrell & Russell, LLP

(57) ABSTRACT

A multimetallic catalyst for hydrogenation of substituted nitroaromatic compounds to give the corresponding aromatic amines. By doping iridium with at least one element from the group manganese, cobalt, iron, nickel, copper and ruthenium, a catalyst is obtained which is characterized by high selectivity.

2 Claims, No Drawings

MULTIMETALLIC CATALYST AND PROCESS FOR PREPARING SUBSTITUTED AROMATIC AMINES

INTRODUCTION AND BACKGROUND

The present invention relates to a catalyst which contains iridium and at least one other doping element on a support for preparing substituted aromatic amines by hydrogenation of the corresponding substituted nitroaromatic compounds. In another aspect, the invention relates to the method of making the catalyst.

The hydrogenation of aromatic nitro compounds with halogen substituents, in particular chlorine, to prepare the corresponding amines has been known for some time (Ullmann, Enzyklopädie der technischen Chemie, 5th edition, vol. A2, page 46 (1985)) and is performed in the presence of metal catalysts using hydrogen as reducing agent. A serious problem in the reaction is the undesired dechlorination of the aromatic compounds, which leads to a reduction in the yield of aromatic amine compound. For this reason, many patents have dealt with processes which attempt to keep the elimination of halogens as low as possible.

Thus, the use of platinum and ruthenium on support materials as shown in U.S. Pat. No. 4,760,187 can lead to an improvement in selectivity, as does the use of platinum, palladium, rhodium, iridium, ruthenium and osmium-containing catalysts which are after-treated with acidic phosphorus compounds (DE-OS 30 06 748).

The activity and selectivity of noble metal catalysts can be affected by the presence of a co-catalyst in the reaction mixture. According to U.S. Pat. No. 5,105,012 iron powder or an iron salt can be added to the reaction mixture as a co-catalyst in addition to palladium on a carbon support as the main catalyst. U.S. Pat. No. 3,253,039 suggests adding silver nitrate to the reaction mixture in addition to a catalyst consisting of platinum on carbon. Silver is then distributed in the entire reaction mixture without being alloyed with the platinum in the catalyst. Lead, copper, nickel, bismuth and chromium nitrate have also been tried as heavy metal additives.

The activity and selectivity of hydrogenation can also be affected by specific doping of a noble metal catalyst with a variety of A and B group elements. Thus, for example, DE 42 36 203 A1 suggests using a platinum catalyst on active carbon doped with nickel and/or cobalt. According to DE 42 18 866 C1, the selectivity of hydrogenation is improved by doping a platinum catalyst on active carbon with copper. In this case, platinum and copper are deposited onto the active carbon support at the same time and then reduced.

Known hydrogenation catalysts are prepared, for example, by introducing the support material into a noble metal salt solution and evaporating the solvent. Optionally, the catalyst is then reduced. As an alternative to this, the support material may also be impregnated with the catalytically active elements by placing the support material in contact with a solution of these elements and precipitating the hydroxides of these elements in an alkaline medium. A reduction procedure may also follow this. Furthermore, it is known that a solution of the noble metal salts may be sprayed onto the support material.

The hitherto known processes for hydrogenation of substituted aromatic nitro compounds, however, still present some problems relating to activity and selectivity. Thus, the use of modifiers or promoters in combination with nitrogen-containing additives during hydrogenation leads to halogenated azobenzene and azoxybenzene derivatives (EP-OS 0 073 105). The formation of such compounds as side-products during the hydrogenation of halogenated nitroaromatic compounds should be avoided due to their toxicity.

An object of the present invention is to provide a catalyst for the hydrogenation of substituted nitroaromatic compounds which is distinguished in particular by improved selectivity as compared with known catalysts.

SUMMARY OF THE INVENTION

The above and other objects of the invention are achieved by a multimetallic catalyst which contains iridium and at least one other promoter on a support. More particularly, the catalyst of the invention features iridium doped with at least one element selected from the group consisting of manganese, cobalt, iron, nickel and ruthenium.

Suitable support materials for the catalyst of this invention are activated carbon or inorganic oxidic materials such as aluminum oxide, titanium dioxide, silicon dioxide or mixed oxides thereof. Activated carbon is preferably used. The activated carbon may be of plant or animal origin and have been activated by a variety of processes (e.g. steam, phosphoric acid, etc.). It may consist of porous and non-porous activated carbon, wherein at least 80 wt. % of the activated carbon particles have a particle size of preferably less than 100 μm. These types of activated carbon are generally obtainable from many different suppliers.

DETAILED DESCRIPTION OF INVENTION

The catalyst according to the invention contains iridium in an amount of from 0.3 to 12, preferably from 0.5 to 7 wt. %, with reference to the support material used, and at least one metal selected from the group consisting of manganese, iron, cobalt, nickel, copper and ruthenium in an amount of from 1 to 100, preferably from 5 to 50 wt. %, with reference to iridium.

To prepare the catalyst, the support as defined herein is first suspended in water and impregnated by adding aqueous salt solutions of the appropriate metals. Then the metals are reduced using a water-soluble reducing agent at temperatures from 0 to 100° C. A different sequence for adding support material, water, metal salt solutions and reducing agent may also be chosen.

Substituted nitroaromatic compounds may be hydrogenated to give the corresponding aromatic amines with high selectivity using the catalyst according to the invention. For this purpose, the nitroaromatic compounds are dissolved in suitable inert solvents and hydrogenated on the catalyst at elevated temperatures with the addition of hydrogen to give amine compounds.

Chlorine substituted aromatic nitro compounds of the formula (I) are preferred for the hydrogenation.

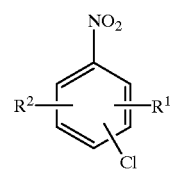

(I)

In formula (I), $R^1$ and $R^2$ may be identical or different and represent hydrogen, an alkyl, alkoxy, hydroxy, carboxy, carbonyl, phenyl or amino group as well as chlorine, fluorine, alkylcarbonylamido or alkyloxycarbonylamido.

Examples of chlorinated aromatic nitro compounds in accordance with formula (I) are 2-nitrochlorobenzene, 3-nitrochlorobenzene, 4-nitrochlorobenzene, 2,4-dichloronitrobenzene, 3,4-dichloronitrobenzene, 2,5-dichloronitrobenzene, 2-chloro-4-nitrobenzene, 4-chloro-3-nitrobenzene, 2-chloro-4-nitroaniline, 2,3,5-trichloronitrobenzene, 2,4,6-trichloronitrobenzene, and isomeric mixtures of the compounds mentioned.

Suitable inert organic solvents for these compounds are aliphatic alcohols such as e.g. methanol, ethanol, isopropanol, butanol or hexanol, carboxylates such as acetic acid and aromatic hydrocarbons such as benzene, toluene and xylene.

Hydrogenation may be performed at temperatures from 40 to 200° C., preferably from 60 to 120° C. and at pressures from 1 to 200, preferably 4 to 150 bar. It is advantageous to perform hydrogenation in the presence of an organic or inorganic basic compound in order to bond optionally eliminated halogen atoms. Triethylamine is preferably used for this, in an amount of 0.05 to 5 wt. %, with reference to the aromatic substituted nitro compound used.

Hydrogenation may be performed either batchwise or continuously. When working continuously, the amount of aromatic nitro compound reactant converted must be replenished and optionally the proportion of basic compound consumed must be made up.

The hydrogenation of substituted aromatic nitro compounds with the catalyst according to the invention is characterized in particular by a high selectivity with regard to possible dehalogenated and other undesired side-products (e.g. azoxybenzene and azobenzene derivatives). In particular, the elimination of chlorine can be almost completely avoided by using the multimetallic catalyst described. In many cases, therefore, additional post-purification of the desired chlorine-substituted aromatic amine compound to remove dechlorinated side-products is unnecessary. This is a clear improvement as compared with the prior art, especially against the background of increasing quality standards.

EXAMPLE 1

94.8 g of activated carbon were suspended in deionized water. To this suspension was added a solution of 20.74 g of hexachloroiridium(IV) acid (23% strength), 0.72 g of manganese(II) chloride tetrahydrate and 0.87 g of sublimated iron (III) chloride. The suspension was adjusted to an alkaline pH of 10 using caustic soda solution, reduced at 80° C. with a freshly prepared sodium borohydride solution (2 wt. %) and filtered after adjusting the pH to 4.

The final catalyst contained 5.0 wt. % of iridium, with reference to the total weight, and 4.2 wt. % of manganese and 6.2 wt. % of iron, with reference to iridium.

EXAMPLE 2

A catalyst was prepared in the same way as described in example 1, using 20.74 g of hexachloroiridium(IV) acid (23% strength) and 1.45 g of sublimated iron(III) chloride.

The final catalyst contained 5.0 wt. % of iridium. with reference to the total weight, and 10.5 wt. % of iron, with reference to iridium.

EXAMPLE 3

20.74 g of hexachloroiridium(IV) acid, 0.404 g of cobalt (II) chloride hexahydrate and 1.16 g of sublimated iron (III) chloride were added to a suspension of 94.8 g of activated carbon in deionized water. The suspension was adjusted to an alkaline pH of 10 using caustic soda solution, reduced with a freshly prepared sodium borohydride solution (2 wt. %) and filtered after adjusting the pH to 4.

The final catalyst contained 5.0 wt. % of iridium, with reference to the total weight, and 2.1 wt. % of cobalt and 8.4 wt. % of iron, with reference to iridium.

EXAMPLE 4

A catalyst was prepared in the same way as described in example 3, using 20.74 g of hexachloroiridium(IV) acid, 1.48 g of nickel(II) nitrate hexahydrate and 0.72 g of manganese(II) chloride tetrahydrate.

The final catalyst contained 5.0 wt. % of iridium, with reference to the total weight, and 6.3 wt. % of nickel and 4.2 wt. % of manganese, with reference to iridium.

EXAMPLE 5

A catalyst was prepared in the same way as described in example 3, using 20.74 g of hexachloroiridium(IV) acid and 3.54 g of ruthenium(III) chloride (14.1% strength).

The final catalyst contained 5.0 wt. % of iridium, with reference to the total weight, and 10.4 wt. % of ruthenium with reference to iridium.

EXAMPLE 6

A catalyst was prepared in the same way as described in example 3, using 20.74 g of hexachloroiridium(IV) acid, 0.438 g of iron(III) chloride and 0.58 g of copper(II) nitrate tetrahydrate.

The final catalyst contained 5.0 wt. % of iridium, with reference to the total weight, and 3.2 wt. % of iron and 3.2 wt. % of copper, with reference to iridium.

COMPARISON EXAMPLE 1

A platinum catalyst doped with copper was prepared in accordance with DE 42 18 866 C1.

100 g of activated carbon were suspended in 800 ml of deionized water. To this suspension was added a solution of 2.5 g of hexachloroplatinic(IV) acid and 0.32 g of copper acetate monohydrate in 200 ml of water. The suspension was heated to 80° C., made alkaline with caustic soda solution and reduced with 0.3 ml of formaldehyde solution (37 wt. %). The suspension was stirred for a further 20 min and then the catalyst was filtered off.

The final catalyst contained 1 wt. % of platinum, with reference to the total weight, and 10 wt. % of copper, with reference to platinum.

COMPARISON EXAMPLE 2

A pure platinum catalyst was prepared in accordance with DE 42 18 866 C1. The preparation procedure was the same as that described in comparison example 1, except that no copper was added.

COMPARISON EXAMPLE 3

A pure iridium catalyst was prepared in accordance with DE 42 18 866 Cl. The preparation procedure was the same as that described in example 1, except that no manganese or iron was added.

APPLICATION EXAMPLE

The catalysts prepared in the preceding examples were tested for activity and selectivity in the high-pressure hydrogenation of 2-chloronitrobenzene.

The hydrogenations took place in a stirred autoclave with a volume of 0.5 l. To determine the catalytic activity and selectivity of the catalysts, the following reaction parameters were kept constant:

|                    |         |
|--------------------|---------|
| Heating-up pressure | 5 bar   |
| Reaction pressure   | 10 bar  |
| Temperature         | 90° C.  |
| Stirring speed      | 700 rpm |

78 g of 2-chloronitrobenzene were quantitatively reacted each time, in the presence of 0.8 mol-% of triethylamine. The end of reaction was recognized by a rapid drop to zero of the hydrogen take-up. The amount of catalyst weighed out each time was 0.385 g. Aniline can be formed in this reaction as a possible dehalogenation product. The proportion of aniline in the product was therefore determined by gas chromatography.

The results of the tests are summarized in the table given below. This shows that the catalysts according to the invention are characterized by high selectivity.

Further variations and modifications of the foregoing will be apparent to those skilled in the art and are intended to be encompassed by the claims appended hereto.

German priority applications 196 29 659.5 and 196 36 214.8 are relied on and incorporated herein by reference.

TABLE

Testing the activity and selectivity of the catalysts

| Catalyst according to example | Solvent | Hydrogenation time [min] | Proportion of aniline [GC %] |
|---|---|---|---|
| Example 1 | Toluene | 45 | <0.05 |
| Example 1 | Methanol | 45 | <0.06 |
| Example 2 | Toluene | 50 | <0.09 |
| Example 2 | Methanol | 55 | <0.08 |
| Example 3 | Toluene | 55 | <0.07 |
| Example 4 | Toluene | 60 | <0.3 |
| Example 5 | Toluene | 40 | <0.2 |
| Example 6 | Toluene | 55 | <0.15 |
| C-Example 1 | Toluene | 30 | 0.9 |
| C-Example 2 | Toluene | 25 | 1.2 |
| C-Example 3 | Toluene | 45 | 0.2 |

We claim:

1. A multimetallic catalyst, consisting of:

a support material, comprising porous or nonporous activated carbon particles, wherein at least 80 wt. % of the activated carbon particles have a particle size of less than 100 μm, 5.0 wt. % iridium by weight of the support material, 4.2 wt. % manganese referenced to the weight of iridium, and 6.2 wt. % iron referenced to the weight of iridium.

2. A mutimetallic catalyst, consisting of:

a support material, comprising porous or nonporous activated carbon particles, wherein at least 80 wt. % of the activated carbon particles have a particle size of less than 100 μm, 5.0 wt. % iridium by the total weight of the multimetallic catalyst, 4.2 wt. % manganese referenced to the weight of iridium, and 6.2 wt. % iron referenced to the weight of iridium.

* * * * *